United States Patent [19]

Martin

[11] Patent Number: 4,636,171
[45] Date of Patent: Jan. 13, 1987

[54] DENTAL POLISHING TIP

[75] Inventor: Thomas W. Martin, North St. Paul, Minn.

[73] Assignee: Minnesota Mining and Manufacturing Company, St. Paul, Minn.

[21] Appl. No.: 768,510

[22] Filed: Aug. 22, 1985

[51] Int. Cl.⁴ .............................................. A61C 3/06
[52] U.S. Cl. ..................................... 433/134; 433/166
[58] Field of Search ..................... 433/142 C, 166, 134

[56] References Cited

U.S. PATENT DOCUMENTS

| 478,881 | 7/1892 | Moore | 433/134 |
| 2,017,881 | 10/1935 | Wiseman | 433/166 |
| 3,858,368 | 1/1975 | Cocherell et al. | 51/358 |
| 4,185,388 | 1/1980 | Jarby | 433/166 |
| 4,447,208 | 5/1984 | Kawai | 433/166 |

OTHER PUBLICATIONS

U.S. patent appln. Ser. No. 170,561, filed 7-21-80 by DuBe and May for "Dental Mandrel & Detachable Abrasive Disk".

Primary Examiner—Robert Peshock
Attorney, Agent, or Firm—Donald M. Sell; James A. Smith; David W. Anderson

[57] ABSTRACT

A polishing tip for use on a mandrel driven by a dental engine includes a cylindrical hollow interior which frictionally engages the mandrel. The cylindrical configuration of the tip interior and the mandrel allows relative slippage if a predetermined torque is exceeded.

6 Claims, 5 Drawing Figures

DENTAL POLISHING TIP

BACKGROUND OF THE INVENTION

1. Field of the Invention

The present invention relates to removable dental polishing tips which may be attached to a rotating mandrel of a dental engine and used for polishing or finishing a surface of a tooth or various prostetic or restorative materials.

2. Description of the Prior Art

U.S. patent application Ser. No. 170,561, filed July 21, 1980 by DuBe and May, and assigned to the assignee of the present application, discloses various mandrels which may be used with a dental engine to grip and rotate abrasive disks. Simply stated, the present invention is an elastomeric tip having various end configurations which may be resiliently deformed to fit over the mandrel and which contracts to grip the mandrel.

U.S. Pat. Nos. 4,185,388 and 4,447,208 disclose dental polishing tips which include asymmetrical cavities designed to engage and be retained on a similarly shaped mandrel. While those tips perform a function which is similar to the tip of the present invention, the positive engagement between the asymmetrical bores of those tips and their associated mandrels permits no relative slippage between the two. This may lead to an unsafe condition wherein the tip, if caught between teeth or gaps in a dental appliance, will continue to be driven by the dental engine and may cause damage or at least discomfort. The asymmetrical bores of the prior tips require manual orientation of the tip relative to the mandrel and may also be difficult to form.

SUMMARY OF THE INVENTION

The dental polishing tip of the present invention includes a hollow cylindrical interior which grips a cylindrical mandrel by frictional engagement. The cylindrical bore is easily formed, allows the tip to rotate relative to the mandrel if caught or obstructed and allows the tip to be assembled to the mandrel in any orientation.

In particular, the dental polishing tip is adapted for use with a mandrel including a cylindrical working end and a reduced diameter driving end coaxial with the working end and includes a body portion having a hollow cylindrical interior of a diameter and length substantially equal to those of the driving end of the mandrel and a reduced diameter cylindrical aperture extending from and coaxial with the hollow interior of the body portion and opening to the exterior surface of the body portion, with the aperture having a diameter substantially equal to that of the working end of the mandrel. The body portion is sufficiently resilient to enable the aperture to be expanded and forced over the working end and to contract and grip the working end to retain the tip on the mandrel.

The polishing tip also includes an end portion which may be any of many various shapes such as conical or cup-shaped and an abrasive may be incorporated into the elastomeric material of the polishing tip to form a self-contained polishing tip.

The mandrel upon which the polishing tip is mounted may be cut with diametral slots to permit the mandrel to expand upon rotation and grip the hollow interior of the polishing tip.

BRIEF DESCRIPTION OF THE DRAWINGS

The present invention will be more thoroughly described with reference to the accompanying drawings, wherein like numbers refer to like parts in the several views, and wherein.

DESCRIPTION OF THE PREFERRED EMBODIMENTS

Figure 1:
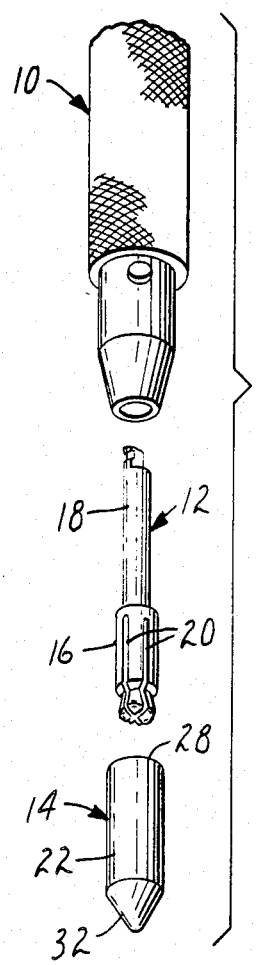
FIG. 1 is an exploded perspective view of a dental engine and a mandrel and polishing tip according to the present invention.

FIG. 1 illustrates a dental engine 10 which is adapted to grip and rotate a mandrel 12 to which may be attached a polishing tip 14 of the present invention. The mandrel 12 is described in many embodiments in U.S. patent application Ser. No. 170,561, filed July 21, 1980 by DuBe and May and assigned to the assignee of the present application. U.S. patent application Ser. No. 170,651 is incorporated herein by reference.

The mandrel 12 includes a generally cylindrical working portion 16 and a reduced diameter driving portion 18 which may be gripped and rotated by the dental engine 10. The working portion 16 is preferably cut by two diametral slots 20 oriented at 90° to each other, although the working portion 16 may be solid or cut by only a single slot, as disclosed in U.S. patent application Ser. No. 170,561.

Figure 2:
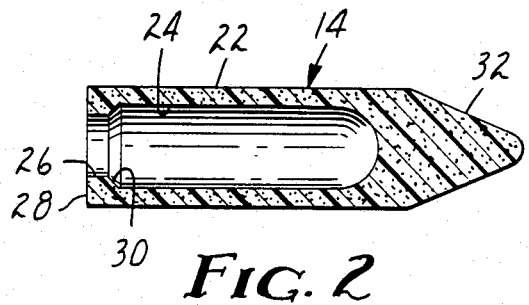
FIG. 2 is a diametral cross-sectional view of a first embodiment of a polishing tip according to the present invention.

As best seen in FIG. 2, the polishing tip 14 includes a body portion 22 which has a hollow cylindrical interior 24 having a diameter and length substantially equal to those of the working portion 16 of the mandrel 12. The body portion 22 of the polishing tip 14 also includes a reduced diameter aperture 26 extending from and coaxial with the hollow interior 24 and opening to the exterior surface 28 of the body portion 22. An angled shoulder 30 is provided between the reduced diameter aperture 26 and the hollow interior 24 to conform to the shape of the mandrel 12, but it should be recognized that the angled shoulder 30 could be eliminated on both the polishing tip 14 and the mandrel 12 and a square corner substituted.

The polishing tip 14 also includes an end portion 32 which is conical in FIG. 2 but which may assume a variety of shapes such as cylindrical, ball-shaped, cup-shaped (as in FIG. 3), or any of an almost endless variety. The only limitation as to the shape of the end portion 32 is that there be sufficient material present to withstand the forces generated by rotation.

The preferred material for the polishing tip 14 is a silicone rubber because of its elastic properties and clinical acceptance. However, it is contemplated that any elastomeric material may be utilized, so long as the material possesses sufficient elastic and strength properties and is safe to use in contact with the human body. The material of the polishing tip 14 may be filled with an abrasive material, as shown in FIG. 2, such as aluminum oxide or zirconium flour to produce a self-contained abrasive unit or a paste containing abrasive particles may be applied to the surface of the end portion 32.

Figure 3:
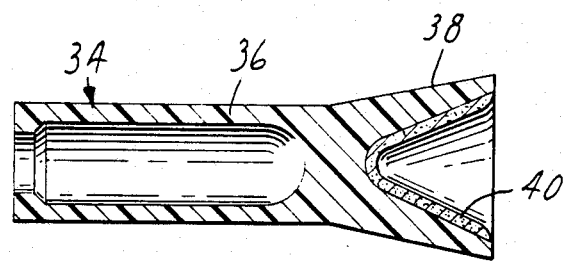
FIG. 3 is a diametral cross-sectional view of a second embodiment of a polishing tip according to the present invention.

FIG. 3 illustrates an alternate embodiment of a polishing tip 34 which includes a body portion 36 having a configuration and features which are identical to those of the body portion 22 of the polishing tip 14 of FIG. 2. FIG. 3 is included to illustrate that an end portion 38 of the polishing tip 34 may assume various configurations and that the material comprising the polishing tip 34 need not include an abrasive. As illustrated in FIG. 3, a paste 40 incorporating an abrasive may be utilized in conjunction with the polishing tip 34.

Figure 4:
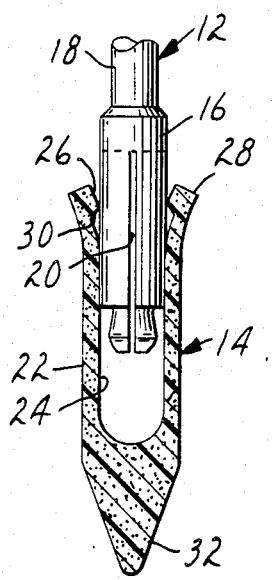
FIG. 4 is a diametral cross-sectional view of the polishing tip in the process of being assembled to the mandrel.
Figure 5:
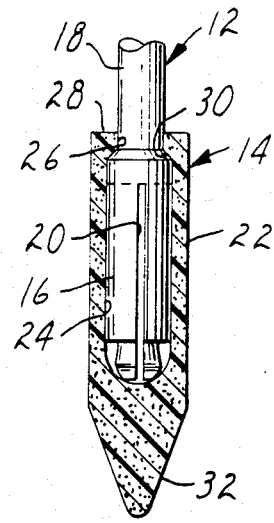
FIG. 5 is a diametral cross-sectional view of the polishing tip as assembled to the mandrel.

FIGS. 4 and 5 illustrate the manner in which the polishing tip 14 (or 34) is attached to the mandrel 12. As stated above, the body portion 22 is formed of a material which is sufficiently resilient to enable the aperture 26 to be expanded and forced over the working portion 16 of the mandrel 12 until the aperture 26 meets the driving portion 18 of the mandrel 12 and contracts to grip the mandrel 12 and retain the polishing tip 14 on the mandrel 12.

If the mandrel 12 is provided with the slots 20, as is preferred, a secondary grip is provided as the mandrel 12 expands due to rotational forces. This, of course, would not be true if the mandrel 12 were solid, in which case friction alone would be relied upon to retain the polishing tip 14.

Since the outer surface of the mandrel 12 and the interior 24 of the polishing tip 14 are both cylindrical, it is possible for the polishing tip 14 to slip and rotate relative to the mandrel 12 if sufficient torque is applied to the polishing tip 14. This relative slippage is a safety feature which allows the polishing tip 14 to stop if the tip 14 becomes trapped in use, such as between two teeth or a gap in a dental appliance. The torque required to produce relative slippage between the polishing tip 14 and the mandrel 12 may be adjusted by varying the diameter of the hollow interior 24 of the polishing tip 14. A slight interference fit between the hollow interior 24 and the mandrel 12 would increase the torque required and a generous tolerance between the hollow interior 24 of the polishing tip 14 and the mandrel 12 would reduce the torque required to arrest movement of the polishing tip. The desirable diameter of the interior 24 of the tip 14 will also depend on whether a solid mandrel 12 is utilized or a diametral cut or cuts 20 are provided. As stated above, diametral cuts 20 in the mandrel 12 will allow expansion of the mandrel 12 upon rotation and provide a secondary grip on the polishing tip 14. In this instance, a higher torque will be required to produce slippage between the polishing tip 14 and the mandrel 12. This torque, of course, could be reduced by increasing the diameter of the interior 24.

Although the present invention has been described with reference to only a limited number of embodiments, it is recognized that many modifications will be apparent to those skilled in the art. All such modifications which fall within the spirit and scope of the appended claims are intended to be included within the invention.

I claim:

1. A dental polishing tip adapted for use with a mandrel including a cylindrical working end and a reduced diameter cylindrical driving end coaxial with said working end, said tip comprising:

a body portion having a hollow cylindrical interior of a diameter and length substantially equal to those of said working end; and a reduced diameter cylindrical aperture extending from and coaxial with said hollow interior and opening to the exterior surface of said body portion, said aperture having a diameter substantially equal to that of said driving end;

said body portion being sufficiently resilient to enable said aperture to be expanded and forced over said working end and to contract and grip said driving end to retain said tip on said working end.

2. A dental polishing tip according to claim 1 wherein said tip includes a solid, conical end portion coaxial with and opposite said aperture with respect to said hollow interior.

3. A dental polishing tip according to claim 2 wherein said body portion and said end portion are formed of an elastomeric material.

4. A dental polishing tip according to claim 3 wherein at least said end portion includes an abrasive embedded within said elastomeric material.

5. A dental polishing tip according to claim 1 wherein said working end further includes at least one diametral slot to permit expansion of said working end upon rotation, said expansion causing said working end to grip said hollow interior of said body portion.

6. A dental polishing tip according to claim 5 wherein said working end includes two diametral slots oriented at 90° to each other.

* * * * *